(12) United States Patent
Schiffman

(10) Patent No.: US 6,406,436 B1
(45) Date of Patent: Jun. 18, 2002

(54) PHYSICAL EXAMINATION INSTRUMENT

(76) Inventor: Noah I. Schiffman, 158 Wentworth St., Apt. 3 Charleston, SC (US) 29401

( * ) Notice: Subject to any disclaimer, the term of this patent is extended or adjusted under 35 U.S.C. 154(b) by 0 days.

(21) Appl. No.: 09/547,581

(22) Filed: Apr. 12, 2000

(51) Int. Cl.[7] ................................................. A61B 5/00
(52) U.S. Cl. ...................................... 600/557; 600/553
(58) Field of Search ............................... 600/552, 553, 600/557, 587, 595

(56) References Cited

U.S. PATENT DOCUMENTS

| | | | | |
|---|---|---|---|---|
| 1,267,554 A | * | 5/1918 | Karatsu | 600/553 |
| 2,532,093 A | * | 11/1950 | Golub et al. | 600/557 |
| 3,185,146 A | * | 5/1965 | Leopoldi | 600/553 |
| 3,515,125 A | * | 6/1970 | Ruskin | 600/553 |
| 4,324,261 A | | 4/1982 | Mark et al. | |
| 4,643,195 A | | 2/1987 | Friedman | |
| 4,825,874 A | * | 5/1989 | Uhleman | 128/710 |
| 4,865,045 A | | 9/1989 | Monreal | |
| 5,222,504 A | | 6/1993 | Solomon | |
| 5,931,793 A | * | 8/1999 | Laudadio | 600/552 |

* cited by examiner

*Primary Examiner*—Max Hindenburg
(74) *Attorney, Agent, or Firm*—Harleston Law Firm; Kathleen M. Harleston (57) ABSTRACT

An instrument for a health practitioner to use in the course of a neurological or physical examination includes: a cylindrical, battery-operated penlight device, a pin prick mechanism, a reflex hammer and/or measuring device, and/or a vibratory mechanism. The pin prick mechanism includes: (a) a removable cylindrical pin dispenser carousel which fits closely over one end of the instrument, and has adjacent pin compartments around the periphery of the pin dispenser carousel, each compartment being capable of loosely holding a straight pin; (b) a recessed band at one end of the instrument, which the pin dispenser carousel fits down over; and (c) a slide mechanism for pushing a portion of a single straight pin from the carousel compartment up through an aperture at the top of the pin dispenser carousel. The pin dispenser carousel is rotatable to a next pin position for repeated use. The reflex hammer mechanism includes: (a) a retractable shaft, which is removably affixed at one end to the instrument, and at an opposite end to (b) a generally disc-shaped reflex hammer head. The reflex hammer head is preferably rotatable and circular, so that it can also be used to measure distance.

24 Claims, 8 Drawing Sheets

PHYSICAL EXAMINATION INSTRUMENT

BACKGROUND OF THE INVENTION

1. Technical Field

The present invention relates in general to instruments for use by health practitioners conducting physical examinations and, more particularly, to a neurological examination instrument that includes a unique reflex hammer and measuring device, pin prick mechanism, penlight device, and/or a vibratory mechanism.

2. Background Information

The modern neurological examination has not changed notably since the 1800s, when the eminent surgeon Dr. Paul Broca discovered the human brain's speech center (now called Broca's area). The modern physician can analyze a CT (computerized tomography), MRI (magnetic resonance imaging), PET (positron emission topology), NCV (nerve conduction velocity), and/or EMG (electromyelogram) studies to confirm which parts of the brain, spinal cord or peripheral nerves are injured or diseased. However, the initial neurological assessment is still conducted using pin pricks, a small light source, touch, a reflex hammer, and a tuning fork, just as it was years ago. These tools are also commonly used in many other aspects of the medical physical examination.

During a neurological examination, the physician tests several aspects of neurological functioning throughout the body. The human nervous system has been mapped out into sensory levels that correspond to vertebral levels of the spinal cord (i.e., cervical, thoracic, etc.). The different sensory modalities of light touch, pain, and vibration are tested for all sensory levels on the right and left sides of the body, and then recorded. In addition, many reflexes (i.e., pupillary, patella, biceps, etc.) are tested to provide information concerning neurological functioning of both the spinal and cerebral areas.

For example, a physician may chart the results of the motor and sensory portions of a neurological examination on an ASIA (American Spinal Injury Association) chart entitled "Standard Neurological Classification of Spinal Cord Injury." The sensory portion of the exam is conducted using a light touch and a pin prick along specific regions of the body, which are pictured on the chart. For example, the right and left "C2" (second cervical) region is touched and pricked. The physician assigns and records scores of 0 (absent) to 2 (normal), depending upon the patient's responses. The motor portion of the examination is similar, with the physician assigning and recording scores for flexion and extension of key muscle groups, e.g., elbow flexors, elbow extensors, and finger abductors.

The present invention is an all-in-one instrument that performs the functions of the traditional tools used for neurological or physical examinations. With this invention, the physician need not spend as much time gathering tools before an exam, halt an exam to seek out a tool, or omit a portion of the exam because the proper tool is not accessible. This instrument includes a unique, sanitary, disposable pin prick mechanism, a retractable reflex hammer mechanism that doubles as a measuring device, a penlight device, and a vibratory mechanism. The pin prick mechanism is used in assessing the patient's "pin prick" sensation in various prescribed locations of the body. The reflex hammer, which extends out for use, is used for testing deep nerve reflexes in addition to doubling as a measuring device. The penlight is shown into the patient's eyes for assessing ipsilateral and contralateral pupillary responses. The instrument's vibratory mechanism replaces a tuning fork for vibratory testing in the course of the neurological exam. Lastly, the instrument's overall compact size allows the health practitioner to carry it in a pocket.

Individual functions of this instrument will prove useful to any health practitioner involved with patient assessment and physical examination. For example, the reflex hammer feature can be used whenever a reflex test is appropriate; the measuring device can be used for measuring wounds or growths; the penlight feature may be used for assessing pupillary constriction in a patient with a possible concussion, etc. The instrument of the present invention is intended to be an indispensable tool for health care workers and a main stay of medical instrumentation for the physical examination.

BRIEF SUMMARY OF THE INVENTION

The present invention is an instrument for a physician or other health practitioner to use in the course of a neurological or physical examination. The instrument comprises: (1) a cylindrical, battery-operated penlight device, (2) a pin prick mechanism, (3) a reflex hammer and/or measuring device, and/or (4) a vibratory mechanism. The pin prick mechanism comprises: (a) a removable cylindrical pin dispenser carousel which fits closely over one end of the instrument, the pin dispenser carousel comprising adjacent pin compartments around the periphery of the pin dispenser carousel, each compartment being capable of loosely holding a straight pin; (b) a recessed band at one end of the instrument, the band's width being approximately equal to the width of the pin dispenser carousel, and the pin dispenser carousel fitting closely down over the band; and (c) a slide mechanism for pushing a portion of a single straight pin from a carousel compartment up through an aperture at the top of the pin dispenser carousel, and temporarily fixing the pin in a stationary position until use, and for pushing the pin completely through the aperture to eject it after use. The pin dispenser carousel is rotatable to a next pin position for repeated use. The reflex hammer mechanism comprises: (a) a retractable shaft, which is removably affixed at one end to the instrument, and at an opposite end to (b) a generally disc-shaped reflex hammer head. The reflex hammer head is preferably rotatable and circular, and can be used to measure distance. The vibratory mechanism and penlight device are preferably connected to the same battery and "on-off" switch.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

In the following description, like reference characters designate like or corresponding parts throughout the several views. Also, in the following description, it is to be understood that such terms as "upper," "lower," "within," and the like are words of convenience and are not to be construed as limiting terms. Referring in more detail to the drawings, the invention will now be described.

Figure 1:
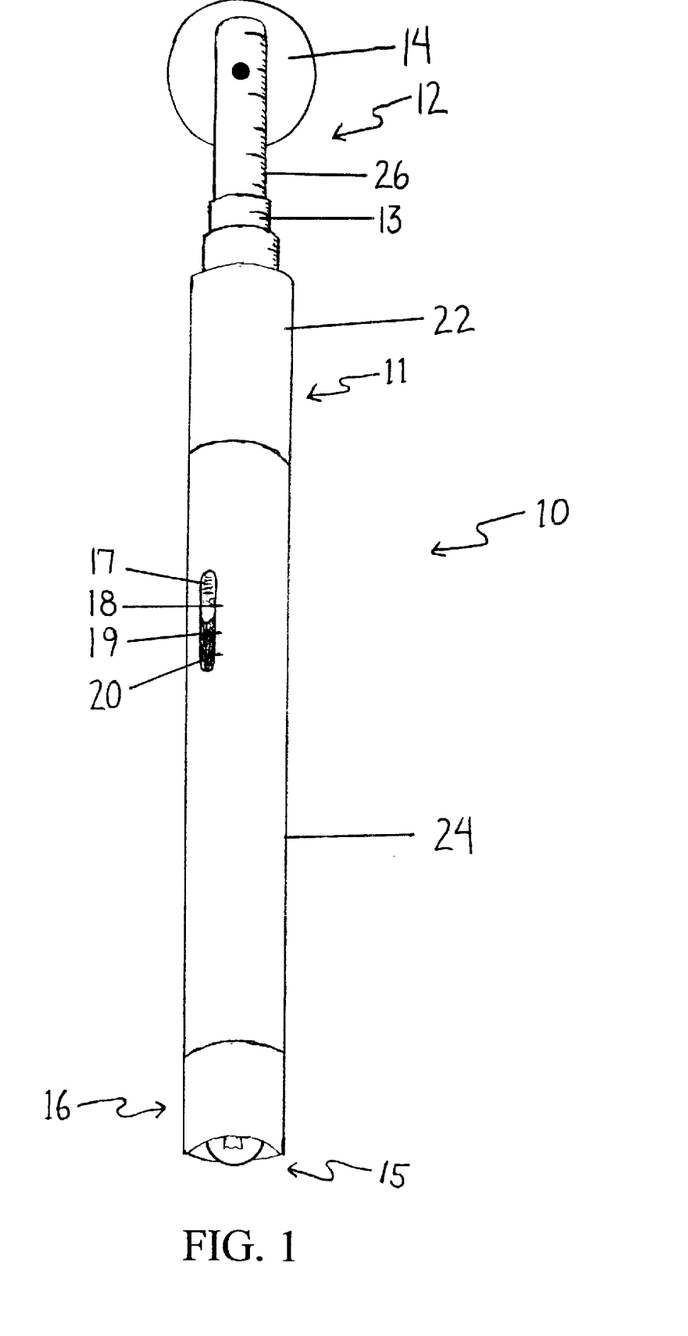
FIG. 1 shows a perspective view of a physical examination instrument according to the present invention.

Referring to FIG. 1, an instrument 10 for conducting a neurological or other type of physical examination is encapsulated by a generally cylindrical housing 11, which is made of a sturdy, lightweight material. The instrument 10 comprises: a reflex hammer mechanism 12, which comprises a retractable shaft 13 with a reflex hammer head 14; a penlight device 15; a pin prick mechanism 16; and a vibratory mechanism. The retractable shaft 13 is removably affixed at one end to the instrument and at an opposite end to the reflex hammer head 14. An "on-off" switch 17 is located approximately at the midpoint of the housing, where it is accessible to the user's thumb. The switch 17 has a first switch setting for "off" 18, a second switch setting 19 for activating the penlight device, and a third switch setting 20 for activating the vibratory mechanism inside the instrument 10.

Figure 2:
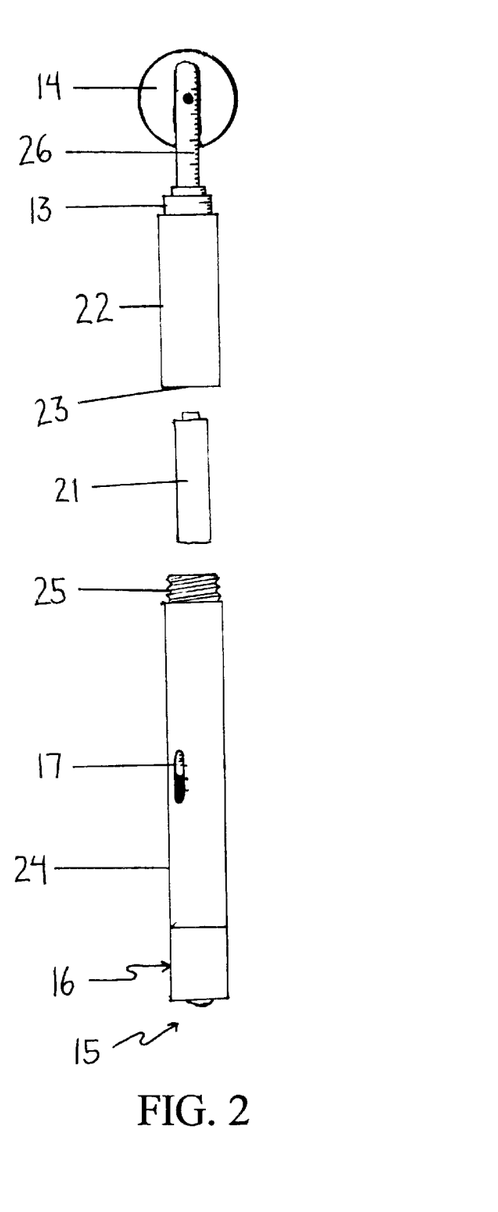
FIGS. 2 and 3 are elevational views of an instrument according to the present invention.
Figure 3:
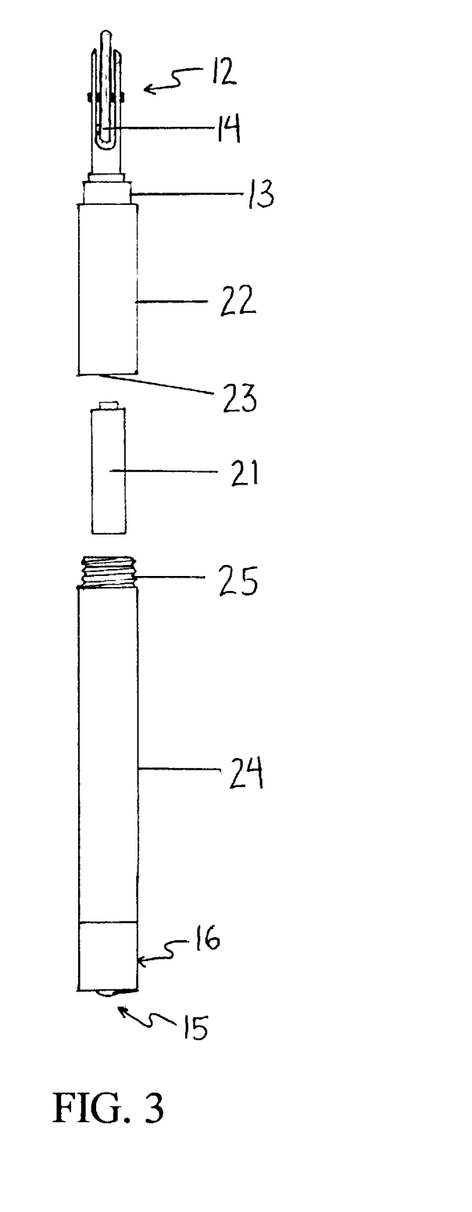

Turning to FIGS. 2 and 3, a preferred embodiment is shown in an open position. Here, the reflex hammer mechanism 12 doubles as a measuring device. The instrument 10 can allow the physician to perform at least five functions useful in a neurological or other physical examination. The housing can be opened, as shown in FIGS. 2 and 3, by the user to replace a battery 21 for the penlight device and the vibratory mechanism. The housing 11 comprises two portions: a reflex hammer portion 22 with a female threaded end 23, and a penlight portion 24 with a corresponding male threaded end 25. The user can unscrew the reflex hammer portion 22 from the penlight portion 24, in order to replace a dead battery 21.

With continued attention to FIGS. 1 and 2, the reflex hammer shaft 13 preferably has a ruler 26 printed on it. When the reflex hammer shaft 13 is in an extended position, the ruler 26 can be used to measure short distances. The measurements are preferably small etched marks on a lightweight metal surface exterior. The calibrated measurements can be continued along the housing itself to extend the length of the ruler. Alternatively, other useful reference information, such as conversion factors, could be printed on the housing. Preferably, each section of the reflex hammer shaft 13 is approximately five (5) centimeters long and the main body of the housing is approximately 15 centimeters in length, thus allowing for approximately 30 centimeters of measurement. English measurement (inches) could easily be etched on the opposite side of the instrument 10 (180 degrees) to allow for a total of 12 inches (one foot) of measurement.

Figure 4:
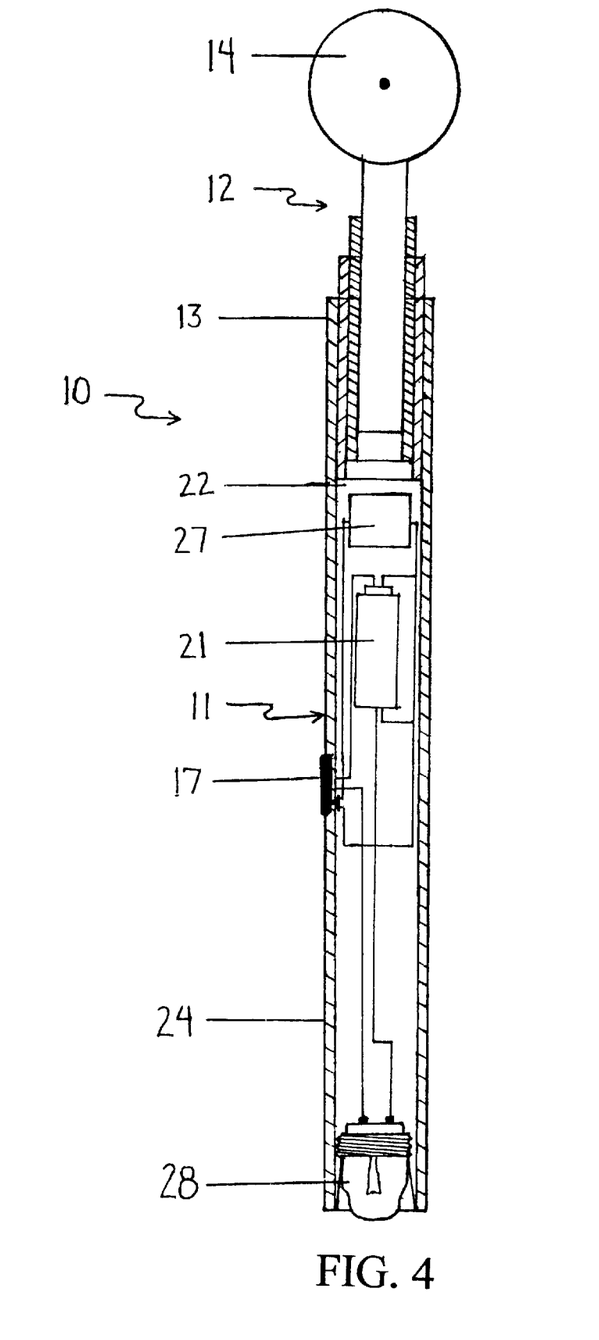
FIG. 4 is an elevational view of the instrument according to FIG. 1, showing the inside of the instrument.

Referring to FIG. 4, a preferred embodiment of the instrument 10 includes a penlight device 15, as well as a vibratory mechanism 27. The penlight device 15 comprises a connection for an incandescent light bulb 28 at the end of the instrument 10. The light bulb fixture is connected to a circuit comprised of the battery 21 and the "on-off" switch 17. Preferably, advancing the switch 17 to the second switch setting 19 from the "off" switch setting 18 completes a circuit in which a 2.2 volt, 0.25 ampere incandescent light bulb is powered by a AA battery. The health practitioner will use the instrument's penlight device, for example, to shine into a patient's eyes to evaluate pupillary reflex. An immediate constriction of both pupils in reaction to the light stimulus is a normal response.

With continued attention to FIG. 4, the vibratory mechanism 27 is also connected in a circuit with the battery 21 and the "on-off" switch 17. This vibratory mechanism is used in place of a conventional tuning fork. In many physical examinations, a tuning fork is required to test a patient's response to vibratory stimulation; however, physicians rarely carry them around. Thus, this portion of a neurological examination is often neglected or postponed.

A tuning fork is roughly "Y" shaped. Ordinarily, the tuning fork is held at its lower end and its upper (forked) end is struck against a surface, such as a table, to initiate vibration. The flat tip of the lower end of the vibrating tuning fork is then placed against the patient's skin. A "normal" response occurs when the patient can detect the vibrations in the areas tested. A lack of perception to vibration stimuli in any areas of the body may indicate neurological impairment. The upper, forked end of the tuning fork is not placed against the patient's skin. This is because the patient would perceive the movement of the oscillations rather than the vibration.

The "on-off" switch 17 has a "vibrate" mode: the third switch setting 20, as shown in FIG. 4. When placed in this mode, a circuit powered by an AA battery is completed, which enables the function of a vibratory element similar to that of pagers and cell phones. The instrument's vibratory mechanism 27 produces a vibration that would be apparent to a normal, healthy individual making contact with the instrument. In other words, this vibratory mechanism preferably vibrates at the same rate as the oscillation rate of a tuning fork. According to previous sensitivity and threshold testing for vibratory stimulation, a vibratory mechanism that oscillates at approximately 512 HZ (hertz) would be optimal and is therefore most preferred herein. The vibratory mechanism is preferably located in the reflex hammer portion of the instrument, which is opposite to the penlight portion. The instrument housing is preferably made of a lightweight aluminum alloy material so that it conducts the vibrations from the vibratory mechanism housed inside the instrument 10 down to the end 29 of the instrument's penlight portion. Once the vibratory mechanism 27 is activated, the penlight end 29 is touched against the patient's skin to test his/her response to the vibratory stimulus. The end 29 of the penlight device is thus analogous to the flat tip of the lower end of a tuning fork. By placing the vibrating end of the instrument at different, prescribed locations on the patient's body, any absence of the stimulus as perceived by the patient may indicate neurological abnormalities with respect to vibratory sensation, at that given region.

The instrument of the present invention has several advantages over a conventional tuning fork. When the practitioner carries the present instrument, she need not go to the extra effort of carrying a number of separate tools (e.g., the tuning fork). The need to strike the tuning fork against a surface is eliminated; the vibratory mechanism is activated with a switch. Also, the patient does not hear when the vibratory mechanism/switch is activated, so it is more difficult for him to consciously or unconsciously "cheat" (i.e., say that he detects a vibration when in fact he does not).

Figure 5:
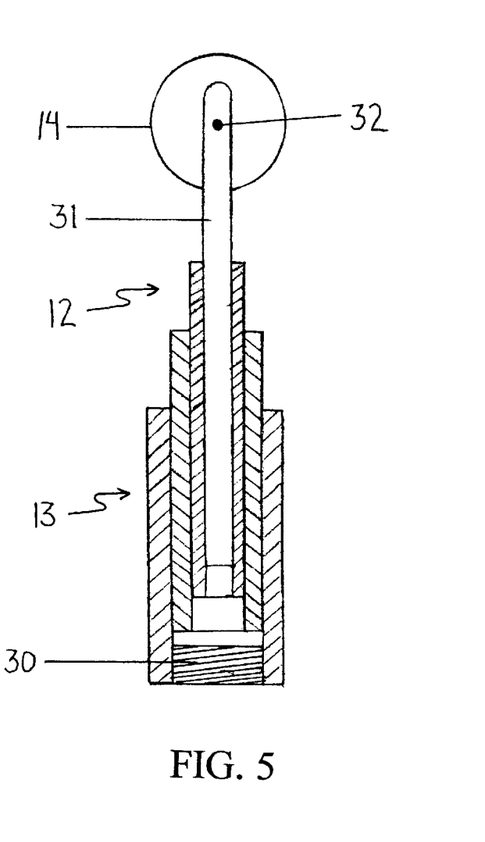
FIG. 5 is a cross-sectional elevational view of a reflex hammer mechanism of an instrument according to the present invention, shown in a retracted position.
Figure 6:
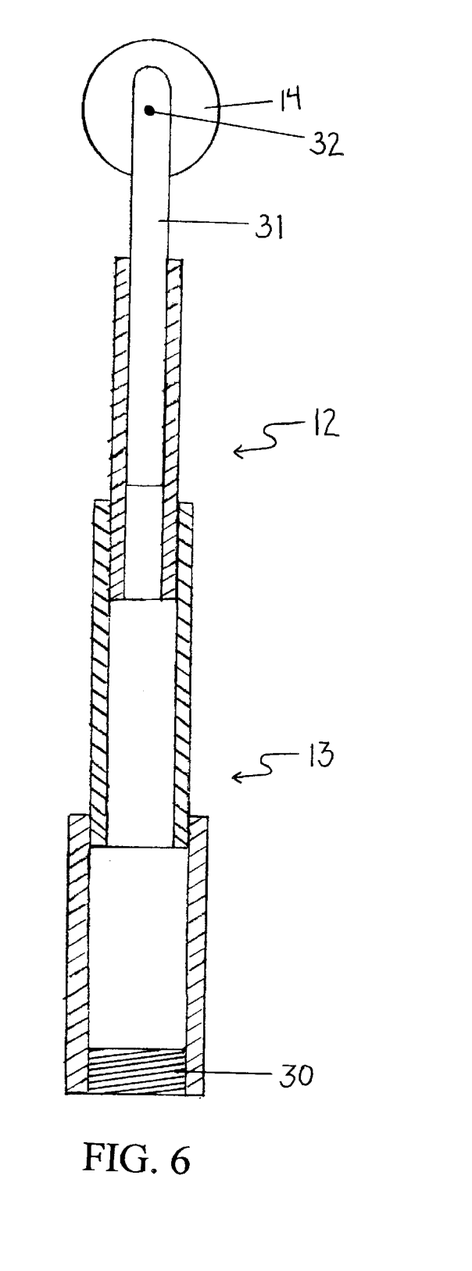
FIG. 6 is a cross-sectional elevational view of the instrument according to FIG. 5, shown in an extended position.

Turning to FIGS. 5 and 6, a retractable reflex hammer mechanism 12 is located opposite to the penlight mechanism 15. In physically examining a patient, a practitioner often strikes overlying tendons in several areas, such as the tendon just below the kneecap, to elicit a reflex arc response. A healthy reflex will cause an involuntary muscle contraction. Many physicians who forget their reflex hammer will omit this portion of the exam. This omission can, on occasion, have adverse consequences.

This reflex hammer mechanism is more versatile than a conventional reflex hammer. Its generally disc-shaped, substantially rubber head 14 is located on the upper end of the shaft 13. The shaft 13 is comprised of concentric cylinders (preferably three) housed on one another. It is not necessary for the head of a reflex hammer to be arrow head-shaped (triangular), as is frequently the case. A narrow striking edge is necessary, and is provided in the present mechanism. This circular head provides a focal point of impact, which accomplishes the task, yet is not unnecessarily painful or intimidating to a young patient. (The hammer head 14 here is substantially comprised of rubber or the like so that the striking edge is relatively soft.) In addition, the concentric cylinders of the shaft 13 are interfitted to allow for retracted (see FIG. 5) and extended (see FIG. 6) positions. The reflex hammer shaft is comprised of between two and five cylinders interfitted on one another. The end of each cylinder that connects with an adjacent cylinder comprises a locking mechanism, and the retractable shaft is capable of being temporarily fixed in an expanded or retracted position. The cylinders of the shaft 13 can be extended by pulling the hammer head 14 until each cylinder end locks into place with the beginning of the cylinder below it. Once the shaft is in the fully extended position, the health practitioner can grasp the penlight portion of the instrument and strike the desired tendinous reflex area with the hammer head 14. The retractable shaft 13 is extended in order to increase the moment arm. A longer moment arm maximizes the force applied, so that a reflex muscle response is elicited. It is easier to carry and store the instrument when the reflex hammer is in the retracted position. The cylinders of the shaft 13 are preferably constructed of a strong, rigid metal, with a thickness sufficient to prevent material fatigue or deformation of the shaft with repeated usage.

With continued attention to FIGS. 5 and 6, there is an internal threaded screw portion 30 at the base of the retractable shaft 13. This allows the user to remove the reflex hammer mechanism to insert the battery. This is an alternative to the opening at the midpoint of the instrument 10, which is shown in FIGS. 2 and 3. The internal threaded screw portion 30 also allows for replacement of the retractable hammer mechanism, in case it is bent or otherwise damaged.

The retracting cylinder at the upper end of the shaft sheaths a substantially solid rod 31, as shown in FIGS. 5 and 6. A pin 32 is inserted transversely through the rod 31 at its upper end.

Figure 7:
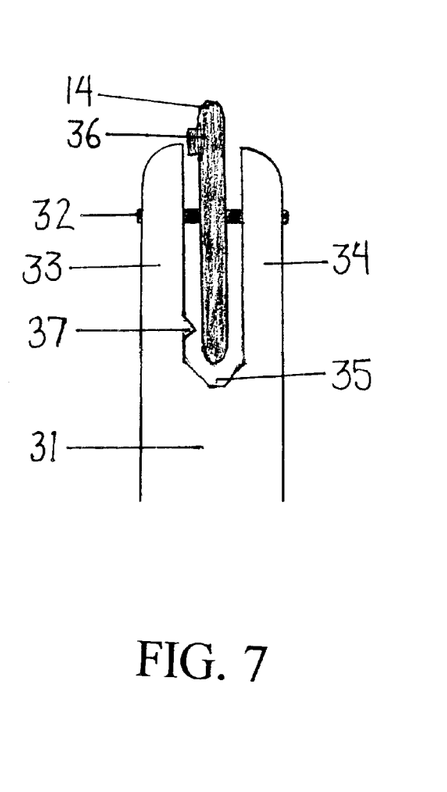
FIG. 7 is an elevational view of a reflex hammer mechanism/measuring device of an instrument according to the present invention.
Figure 8:
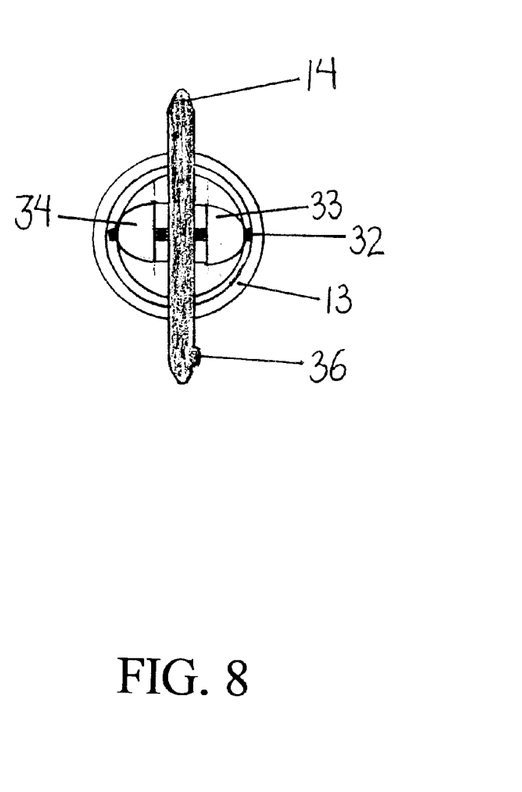
FIG. 8 is a plan view of the instrument according to FIG. 7.

As shown in FIGS. 7 and 8, the rod 31 is divided at its upper end into two matching arms 33, 34 with a space between them. The pin 32 extends through the first arm 33, through the center of the hammer head 14, and through the second arm 34. The space between the arms is well 35. The well is slightly wider than the head and accommodates movement of the head. The circular head 14 preferably rotates about the pin 32 within the wheel well 35. The pin 32 preferably fits through a grommet inserted at the center of the head 14, to facilitate movement of the head about the pin. Importantly, the rotatable head serves as a measuring device in the present invention. The reflex hammer head doubles as the wheel of the measuring device.

Most physicians do not carry a tape measure around with them. They often take measurements using a short ruler printed on the cover of one of a reference manual carried with them. Normally, these manuals/rulers are approximately five inches long, which results in difficulty in measuring limbs, etc. The measuring device 14 of this instrument is useful for measuring limb length discrepancies, extremity circumference, or for any other application in which distance is measured. For example, some patients have one leg shorter than the other, causing gait abnormalities or a pelvic tilt.

Continuing to refer to FIG. 7, the measuring device comprises the rubber head 14, which comprises a small wheel tab 36 (an evagination) along an inner edge of the head/wheel. The wheel tab is preferably squared off, as shown in FIG. 7. An arm tab 37 projects out toward the rubber head in the well 35 from the inside of the first arm. It is preferably pointed, as shown in FIG. 7. With each rotation of the head 14 around the pin 32, the wheel tab 36 strikes the corresponding arm tab 37. The wheel tab 36 is the same distance from the center of the circular head as the arm tab 37 is from the center of the head. In use, the user grasps the penlight portion of the instrument 10 and places the head at the start of the area of the patient's body that is to be measured. The user than wheels the hammer head 14 in a line along the area to be measured. The head is rubber, so friction causes it to turn as it is rolled along on the patient's skin. With each rotation of the rubber head 14, the wheel tab 36 snaps across the arm tab 37, creating a "click" sound. The practitioner counts the number of rotations by counting the clicks he hears. Since the hammer head/measuring wheel 14 is a known diameter, the distance the head/wheel has traveled along the patient's skin can be quantified. The head/wheel most preferably has a diameter of 3.18 centimeters, providing a wheel circumference of ten centimeters. One click is therefore equivalent to ten centimeters. For a body area longer than about six or seven inches, this measuring device is easier to use than a straight edge ruler. Also, it is not necessary to carry and hunt for a separate ruler, when the present instrument, which is probably already in the practitioner's hand, can be used so easily.

In summary, the reflex hammer head is suspended in a well 35 between two corresponding shaft arms at the head end of the retractable shaft. The reflex hammer mechanism comprises a pin which is affixed at its opposite ends to the two shaft arms. The pin passes through a grommet at the center of the reflex hammer head, and the reflex hammer head is rotatable on the pin. Preferably, the reflex hammer head comprises a head tab 36 along an inner edge of the reflex hammer head, and a corresponding arm tab 37 along an inside of one shaft arm. The head tab 36 strikes the arm tab 37 each time the reflex hammer head makes one rotation about the pin, and the striking of the head tab on the shaft arm tab emits an audible sound. The practitioner rolls the reflex hammer head along the part to be measured, counts the number of sounds, or clicks, that are emitted, and calculates the distance trarveled by the head.

The sensory portion of a neurological exam is conducted with a light touch and a pin prick along specific regions of the body, as described above. The physician frequently carries a safety pin for this part of the assessment. The practitioner might also use a pin for other physical assessments, such as pricking the bottom of a diabetic patient's foot to test sensation. For many years, it has been the practice of many physicians to use one unsterilized pin on several patients in the course of a work day. Given our present knowledge of the blood transmission of certain infectious diseases (even a droplet), it would seem prudent to use a separate, clean pin for each patient, and sometimes a separate pin for different parts of the body. The present novel pin prick mechanism is safer and more sanitary than a single pin that is reused on different patients.

Figure 9:
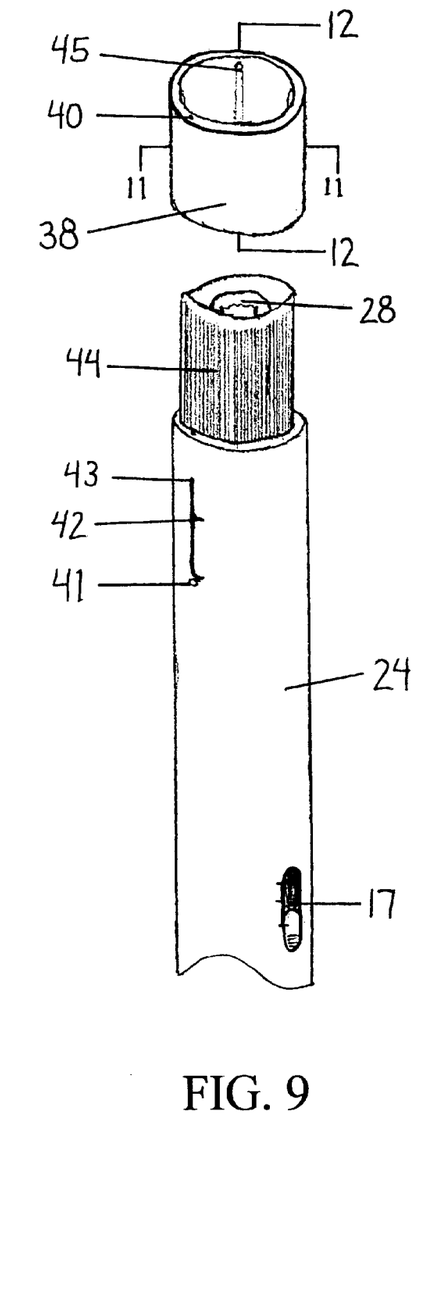
FIG. 9 is a perspective view of a penlight device/pin prick mechanism of an instrument according to the present invention, shown in an open position.
Figure 10:
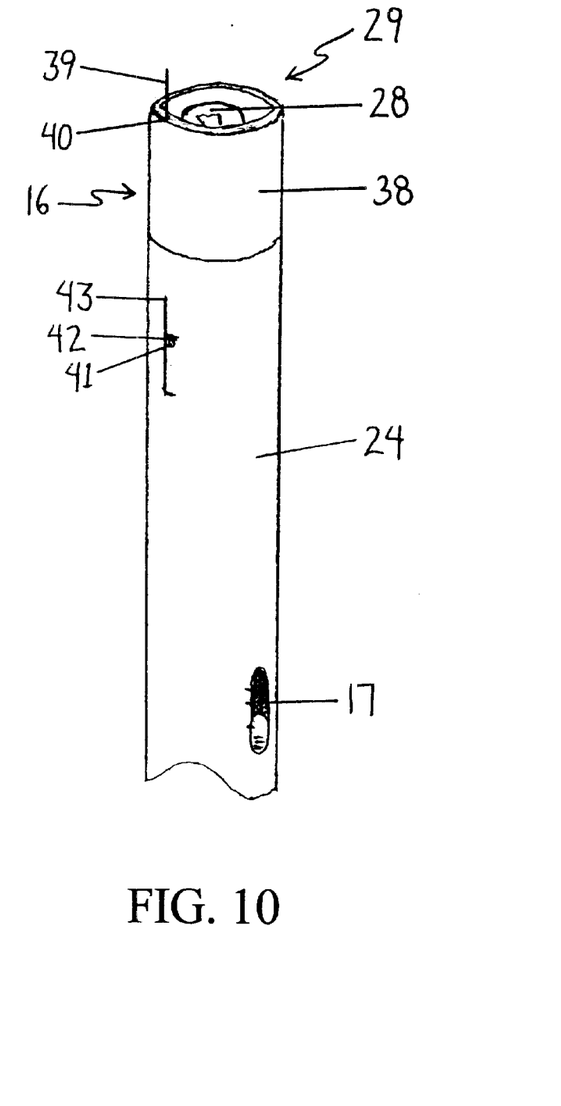
FIG. 10 is a perspective view of the instrument according to FIG. 9, shown in a closed position.

FIGS. 9–16 illustrate preferred pin prick mechanisms 16. Referring to FIGS. 9 and 10, the novel pin prick mechanism 16 of the present instrument is shown with a detached pin dispenser carousel 38 in FIG. 9, and an affixed pin dispenser carousel in FIG. 10. In FIG. 10, a single, new pin 39 extends out from one point along the periphery of the pin dispenser carousel 38 at the penlight end 29 of the instrument 10. The pin extends through a pin aperture 40 at the upper edge of the pin dispenser carousel 38. Each new pin 39 is pushed out through the pin aperture 40 by a slide button 41. In FIG. 9, the slide button is shown at a first position, where no pin projects from the aperture 40. When the user wishes to conduct a pin prick test, (s)he pushes the slide button with a thumb to a second, "ready" position 42. In this position, the pointed end of a pin projects from the aperture 40. This is shown in FIG. 10. The slide button at a third position 43 is used to eject a used pin from the aperture 40 into a suitable trash receptacle.

Continuing with FIG. 9, the cylindrical pin dispenser carousel 38 fits down over a cylindrical band 44. At the center of the cylindrical band 44 is the penlight bulb 28 of the penlight device 15. A vertical tab 45 extends along an inside wall of the cylindrical pin dispenser 38.

Figure 11:
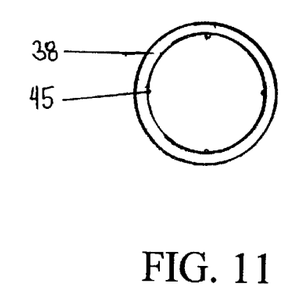
FIG. 11 is a cross-sectional plan view of the pin dispenser of the instrument, taken along line 11—11 of FIG. 9.
Figure 12:
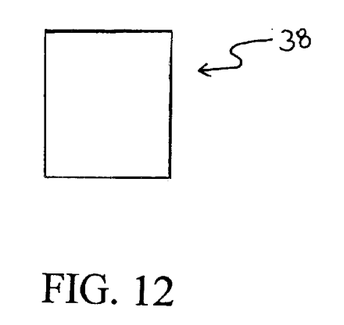
FIG. 12 is a cross-sectional, elevational view of the pin dispenser of the instrument, taken along line 12—12 of FIG. 9.
Figure 13:
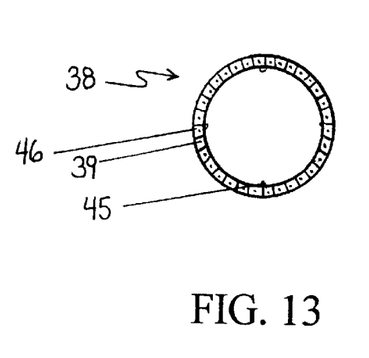
FIG. 13 is a plan view of the pin dispenser according to FIG. 9.
Figure 14:
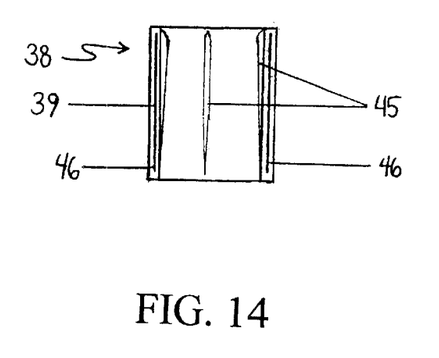
FIG. 14 is an elevational view of the pin dispenser according to FIG. 9.

In FIGS. 11 and 12, cross-sections (horizontal and vertical) of the pin dispenser carousel 38 are shown. FIG. 13 shows the pin dispenser carousel from the top, and FIG. 14 shows the pin dispenser carousel from the outside. As shown in FIGS. 11 and 12, individual compartments 46 in series around the periphery of the carousel hold individual pins 39. As seen in FIGS. 11, 12 and 13, the pin dispenser carousel 38 has four elongated vertical tabs 45 evenly spaced along the inside of the carousel. These vertical tabs fit down over four of the grooves in the cylindrical band 44, which surrounds the penlight bulb 28 (see FIG. 9).

In summary, the pin prick mechanism comprises:
(a) a removable cylindrical pin dispenser carousel 38, which fits closely over one end of the instrument 10, the pin dispenser carousel comprising a plurality of adjacent pin compartments 46 around the periphery of the pin dispenser carousel, each compartment being capable of loosely holding a straight pin 39. The interior of the cylindrical pin dispenser carousel comprises between about two and ten, most preferably four, vertical tabs 45.
(b) a recessed band 44 at one end of the instrument, the band's width being approximately equal to the width of the pin dispenser carousel, and the pin dispenser carousel 38 fitting closely down over the band. The band preferably comprises a plurality of vertically oriented band grooves that are adjacent to one another around the circumference of the band, the cylindrical pin dispenser carousel comprises an interior facing which comprises at least two vertically oriented tabs 45, and the band grooves correspond to the vertically oriented tabs.
(c) a slide mechanism 47 for pushing a portion of a single straight pin 39 from the carousel compartment up through an aperture 40 at the top of the pin dispenser carousel, and temporarily fixing the pin in a stationary position until use, and for pushing the pin completely through the aperture to eject it after use.

Once a pin has been used and ejected, the pin dispenser carousel is rotatable to a next pin position for repeat use. This is done by lifting the pin dispenser carousel slightly and rotating it slightly until a click is felt, then sliding the vertical tabs on the pin dispenser carousel down into the next grooves on the grooved projection. The sliding button can now be used to push the next pin through the aperture.

Figure 15:
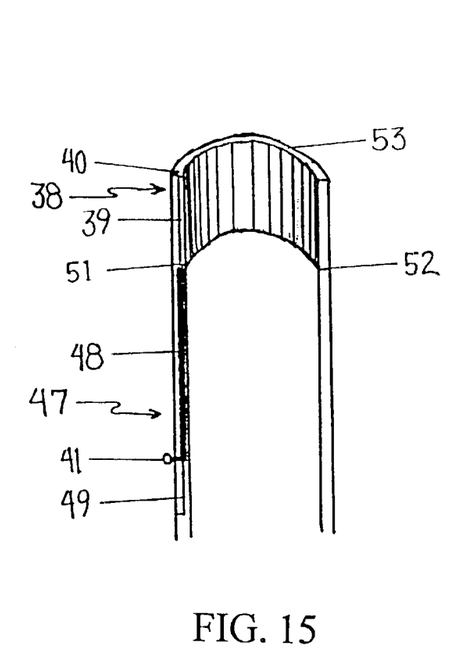
FIG. 15 is a perspective view of a cross section of a pin dispenser mechanism of an instrument according to the present invention, with a pin in a sheathed position.
Figure 16:
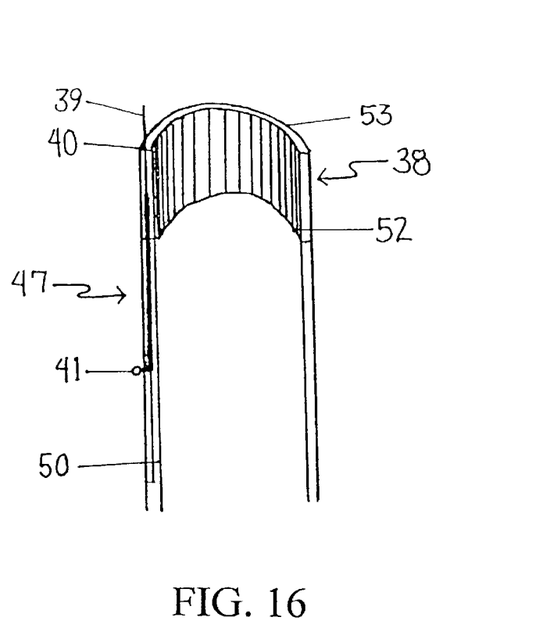
FIG. 16 is a perspective view of a cross section of a pin dispenser mechanism of an instrument according to the present invention, with a pin in a ready position.
Figure 17:
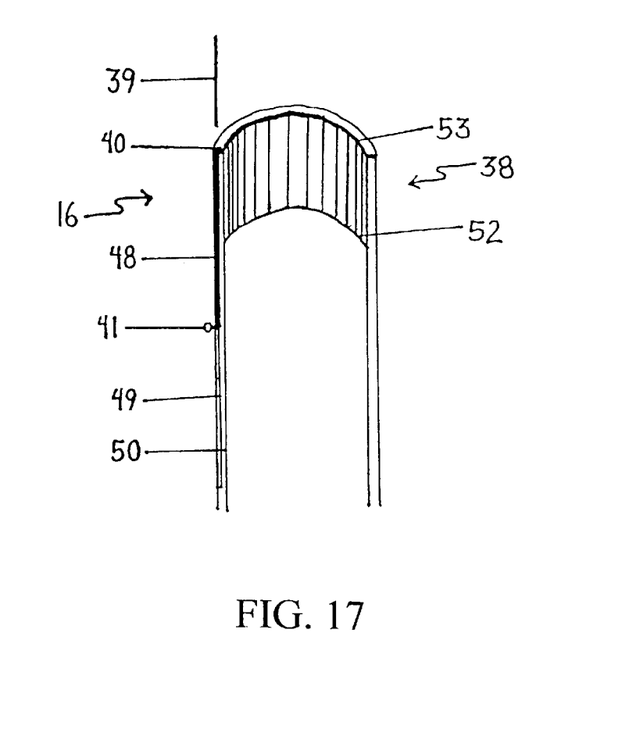
FIG. 17 is a perspective view of a cross section of a pin dispenser mechanism of an instrument according to the present invention, with an ejected pin.

Referring to FIGS. 15 and 16, the slide mechanism 47 is preferably comprised of: (1) a slidable rod 48 with a slide button 41 at one end, the slide button being accessible to the user and slidable along a slide button track 49 in the housing; (2) a slide shaft 50 along the housing, the slidable rod being closely fitted in a shaft in the housing; an opposite end of the rod being positioned adjacent to a base of a pin in a compartment of the pin dispenser carousel. The slidable rod slides along the slide shaft 50. A second aperture 51 allows a portion of the slidable rod 48 to extend through into the pin dispenser carousel. The slide button has a first position at an end of the track for a sheathed pin (see FIG. 15), a second position 42 along a midpoint of the track for pushing a portion of the pin through the aperture (see FIG. 16), and a third position 43 at an opposite end of the track for ejecting the pin through the aperture, as shown in FIG. 17.

Preferably, the penlight device 15 and the pin prick mechanism 16 are at the same end of the instrument, and the pin dispenser carousel 38 surrounds a well that holds the penlight bulb 28.

As shown in FIGS. 15 and 16, the pin dispenser carousel 38 is preferably disposable and further comprises a paper covering 52 along the bottom of the carousel, and a penetrable rubber or rubber-like covering 53 at the top of the carousel. The paper covering holds the pins in place in the pin dispenser carousel, yet the sliding rod easily perforates the paper covering. The rubber (includes rubber-like materials) covering on the top of the pin dispenser carousel contains the pins in the compartments, yet the individual pins can easily be pushed through the rubber covering by the force of the user's thumb on the sliding rod in the slide mechanism.

With this pin dispenser carousel, a new, clean pin is available for each patient/use. The present pin prick mechanism has several advantages. The pin only projects a short distance from the end of the instrument, so the practitioner is prevented by the rounded end of the penlight from inserting the pin very deeply into the patient's skin. Secondly, possible contamination of the pin by contact with a practitioner's hand is avoided because the practitioner does not touch the pin. Thirdly, contamination/disease is not spread from one patient to the next with the present pin prick mechanism because the same pin is not used repeatedly on several patients. Fourth, where a pin has inadvertently been contaminated with an ill patient' blood, any potential danger to the physician, other healthcare workers, or other patients from an accidental prick by the pin is avoided. The pin can be ejected from the instrument of the present invention without contacting the pin. Care must be taken to eject the pin into an appropriate waste receptacle.

From the foregoing it can be realized that the described device of the present invention may be easily and conveniently utilized as a five-in-one neurological examination instrument. The handy, inexpensive instrument of the present invention obviates the need for a physician to have separate, independent tools. In fact, the present instrument in some cases performs better than separate, conventional, physician's examining tools.

While preferred embodiments of the invention have been described using specific terms, this description is for illustrative purposes only. It is to be understood that any dimensions given herein are also illustrative, and are not meant to be limiting. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. An instrument for use by a health practitioner during a physical examination, the instrument comprising a pin prick mechanism, the pin prick mechanism comprising:
   (a) a removable cylindrical pin dispenser carousel which fits closely over one end of the instrument, the pin dispenser carousel comprising a plurality of adjacent pin compartments around the periphery of the pin dispenser carousel, each compartment being capable of loosely holding a straight pin;
   (b) a recessed band at one end of the instrument, the band's width being approximately equal to the width of the pin dispenser carousel, and the pin dispenser carousel fitting closely down over the band; and
   (c) a slide mechanism for pushing a portion of a single straight pin from the carousel compartment up through an aperture at the top of the pin dispenser carousel, and temporarily fixing the pin in a stationary position until use, and for pushing the pin completely through the aperture to eject it after use; and wherein the pin dispenser carousel is rotatable to a next pin position for repeated use.

2. An instrument according to claim 1, further comprising a cylindrical, battery-operated penlight.

3. An instrument according to claim 2, wherein the penlight device and the pin prick mechanism are at the same end of the instrument, the pin dispenser carousel surrounding a well that holds a penlight bulb.

4. An instrument according to claim 3, further comprising a reflex hammer mechanism at an end of the instrument opposite to the penlight device, the reflex hammer mechanism comprising: (a) a retractable shaft, and (b) a generally disc-shaped reflex hammer head; the retractable shaft being removably affixed at one end to the instrument, and affixed at an opposite end to the reflex hammer head.

5. An instrument according to claim 4, wherein the pin dispenser carousel is disposable and further comprises a paper covering along the bottom of the carousel, and a penetrable natural or synthetic rubber covering at the top of the carousel; and wherein the band comprises a plurality of vertically oriented band grooves that are adjacent to one another around the circumference of the band, the cylindrical pin dispenser carousel comprises an interior facing which comprises at least two vertically oriented tabs, and the band grooves correspond to the vertically oriented tabs.

6. An instrument according to claim 5, wherein the slide mechanism is comprised of: (1) a slidable rod with a slide button at one end, the slide button being accessible to the user and slidable along a track in a housing of the instrument; (2) a shaft along the instrument housing, the slidable rod being closely fitted in the shaft in the instrument housing; an opposite end of the rod being positioned adjacent to a base of a pin in the compartment of the pin dispenser carousel; and wherein the slide button has a first position at an end of the track for a sheathed pin, a second position along a midpoint of the track for pushing a portion of the pin through the aperture, and a third position at an opposite end of the track for ejecting the pin through the aperture.

7. An instrument according to claim 6, wherein the reflex hammer shaft is comprised of between two and five cylinders interfitted on one another; wherein the end of each cylinder that connects with an adjacent cylinder comprises a locking mechanism; and wherein the retractable shaft is capable of being temporarily fixed in an expanded or retracted position.

8. An instrument according to claim 5, wherein the reflex hammer head is rotatable and circular, and wherein the reflex hammer mechanism is capable of being used to measure distance.

9. An instrument according to claim 8, the instrument further comprising an electronic vibratory mechanism capable of use for testing a person's response to a vibratory stimulus.

10. An instrument according to claim 8, wherein the penlight and the vibratory mechanism are powered by the same battery and are turned on and off by the same switch.

11. An instrument for use by a health practitioner during a physical examination, the instrument comprising a retractable reflex hammer mechanism, the reflex hammer mechanism comprising: (a) a retractable shaft, and (b) a generally disc-shaped, rotatable reflex hammer head; the retractable shaft being removably affixed at one end to the instrument, and affixed at an opposite end to the reflex hammer head; the retractable shaft comprising two corresponding shaft arms at its head end forming a well between them; the hammer head being rotatably suspended in the well parallel to the longitudinal axis of the shaft arms; the reflex hammer mechanism being audible and adapted for measuring distance.

12. An instrument according to claim 11, further comprising a cylindrical, battery-operated penlight.

13. An instrument according to claim 12, wherein the reflex hammer mechanism comprises a pin affixed at its opposite ends to the two shaft arms; the pin passing through a grommet at the center of the reflex hammer head; the reflex hammer head being rotatable on the pin.

14. An instrument for use by a health practitioner during a physical examination, the instrument comprising a retractable reflex hammer mechanism, the reflex hammer mechanism comprising: (a) a retractable shaft, and (b) a generally disc-shaped, rotatable reflex hammer head; the retractable shaft being removably affixed at one end to the instrument, and affixed at an opposite end to the reflex hammer head; the circular reflex hammer head being suspended in a well between two corresponding shaft arms at the head end of the retractable shaft; the reflex hammer mechanism further comprising a pin affixed at its opposite ends to the two shaft arms; the pin passing through a grommet at the center of the reflex hammer head; the reflex hammer bead being rotatable on the pin; wherein the reflex hammer mechanism comprises a head tab along an inner edge of the reflex hammer head, and a corresponding shaft arm tab along an inside of one shaft arm; and wherein the head tab strikes the shaft arm tab each time the reflex hammer head makes one rotation about the pin, and wherein the striking of the head tab on the shaft arm tab emits an audible sound.

15. An instrument according to claim 14, wherein the reflex hammer shaft is comprised of between two and five cylinders telescoped on one another, and wherein the retractable shaft is capable of being temporarily fixed in an expanded or retracted position.

16. An instrument according to claim 14, further comprising a disposable pin prick mechanism.

17. An instrument according to claim 16, wherein the pin prick mechanism comprises a disposable, rotatable pin dispenser carousel at one end of the instrument; the pin dispenser carousel houses pins in separate compartments of the carousel; and the pin prick mechanism is capable of presenting a clean pin for use on each patient.

18. An instrument for use by a health practitioner during a neurological examination of a patient, the instrument comprising an electronic vibratory mechanism capable of producing vibrations that would be apparent to a normal, healthy individual making contact with the instrument; and a disposable pin prick mechanism comprising a disposable, rotatable pin dispenser carousel at one end of the instrument; the pin dispenser carousel housing individual, disposable pins.

19. An instrument according to claim 18, wherein the vibratory mechanism is connected in a circuit with a battery and an "on-off" switch, and wherein a housing around the instrument comprises a conductive metal.

20. An instrument according to claim 19, further comprising a cylindrical, battery-operated penlight.

21. An instrument for use by a health practitioner during a neurological examination of a patient, the instrument comprising an electronic vibratory mechanism adapted for producing perceptible vibrations, and an instrument housing comprising a conductive metal; the vibratory mechanism being connected in a circuit with a battery and an "on-off" switch; the instrument further comprising a disposable pin prick mechanism and a cylindrical, battery-operated penlight; wherein the penlight and the vibratory mechanism share the battery and the "on-off" switch; and wherein the vibratory mechanism oscillates at at about 512 HZ when the "on-off" switch is activated by a user.

22. An instrument according to claim 21, further comprising a retractable reflex hammer mechanism, the reflex hammer mechanism comprising: (a) a retractable shaft, and (b) a generally disc-shaped reflex hammer head; the retractable shaft being removably affixed at one end to the instrument, and affixed at an opposite end to the reflex hammer head.

23. An instrument according to claim 22, wherein the pin prick mechanism comprises a disposable, rotatable pin dispenser carousel at one end of the instrument; the pin dispenser carousel houses pins in separate compartments of the carousel; and the pin prick mechanism is capable of presenting a clean pin for use on each patient.

24. An instrument according to claim 22, wherein the reflex hammer head is rotatable, circular and suspended in a well between two corresponding shaft arms at the head end of the retractable shaft; the reflex hammer mechanism comprises a pin which is held at its opposite ends by the two shaft arms; the pin passes through a grommet at the center of the reflex hammer head; the reflex hammer head is rotatable on the pin; the reflex hammer head comprises a head tab along an inner edge of the reflex hammer head, and a corresponding shaft arm tab along an inside of one shaft arm; the head tab strikes the shaft arm tab each time the reflex hammer head makes one rotation about the pin; the striking of the head tab on the shaft arm tab emits an audible sound; and the reflex hammer mechanism is capable of being used to measure distance.

* * * * *